United States Patent
Hirai et al.

[11] Patent Number: 5,882,935
[45] Date of Patent: Mar. 16, 1999

[54] ANALYSIS ELEMENT AND METHOD FOR ANALYZING GLYCATED HEMOGLOBIN CONTENT RATIO

[75] Inventors: Kikuo Hirai; Hiroshi Shinoki; Masashi Ogawa; Yoshihiko Makino, all of Saitama, Japan

[73] Assignee: Fuji Photo Film Co., Ltd., Kanagawa, Japan

[21] Appl. No.: 544,133

[22] Filed: Oct. 17, 1995

[30] Foreign Application Priority Data

Oct. 19, 1994 [JP] Japan .................................. 6-278645

[51] Int. Cl.$^6$ ....................... H01L 21/302; H01L 21/304; H01L 21/306; H01L 21/76
[52] U.S. Cl. ........................... 436/67; 435/7.9; 435/7.91; 435/28.2; 435/28; 436/66; 436/523; 422/82.05
[58] Field of Search ............................... 435/7.9, 287.27, 435/7.91, 28; 436/66, 67, 523; 422/82.05

[56] References Cited

U.S. PATENT DOCUMENTS 5,093,081  3/1992  Sudo et al. .

FOREIGN PATENT DOCUMENTS

| | | |
|---|---|---|
| 2090981 | 3/1993 | Canada . |
| 0451848 | 10/1991 | European Pat. Off. . |
| 0503459 | 9/1992 | European Pat. Off. . |
| 0559164 | 9/1993 | European Pat. Off. . |

OTHER PUBLICATIONS

Database WPI—Section Ch, Week 9224—Derwent Publication & JP A 04 128 655 (Fuji Photo Film Co. Ltd.).

*Primary Examiner*—Paula K. Hutzell
*Assistant Examiner*—Heather A. Bakalyar
*Attorney, Agent, or Firm*—McAulay Nissen Goldberg Kiel & Hand, LLP

[57] ABSTRACT

An analysis element for analyzing both amounts of glycated hemoglobin and total hemoglobin in an aqueous liquid sample to determine glycated hemoglobin content ratio in the sample. The element comprises a substrate layer for receiving a reaction mixture after the completion of an immunological reaction between the glycated hemoglobin in the sample and an enzyme-labelled antibody against the glycated hemoglobin, and a reagent layer. The substrate layer contains a non-diffusible substrate which forms a diffusible material in the presence of the enzyme of the enzyme-labelled antibody, the activity of the enzyme being effected relative to the steric hindrance due to the immunological reaction. The reagent layer contains a reagent composition for reacting with the diffusible material to form a dye detectable colorimetrically in a wavelength range which is not effected by an absorption spectrum of the hemoglobin. The total hemoglobin retained in the substrate layer and the dye formed in the reagent layer are colorimetrically analyzed separately, and the glycated hemoglobin content ratio is calculated from respective values. An analysis method using this analysis element is also provided.

16 Claims, 5 Drawing Sheets

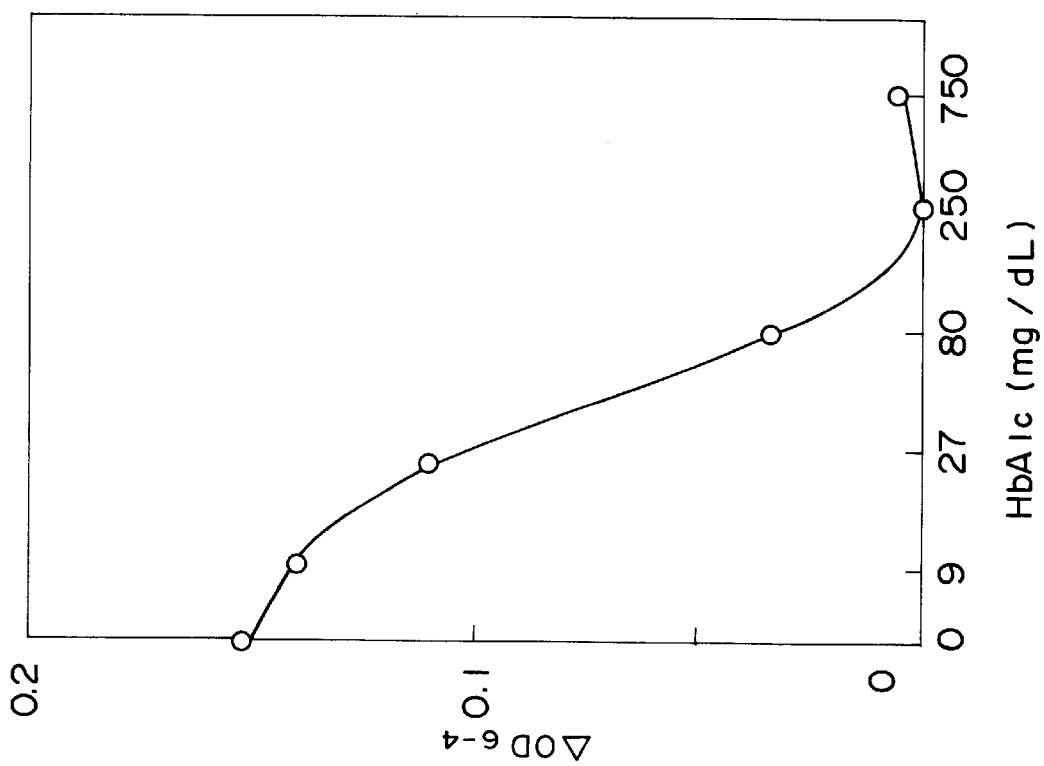
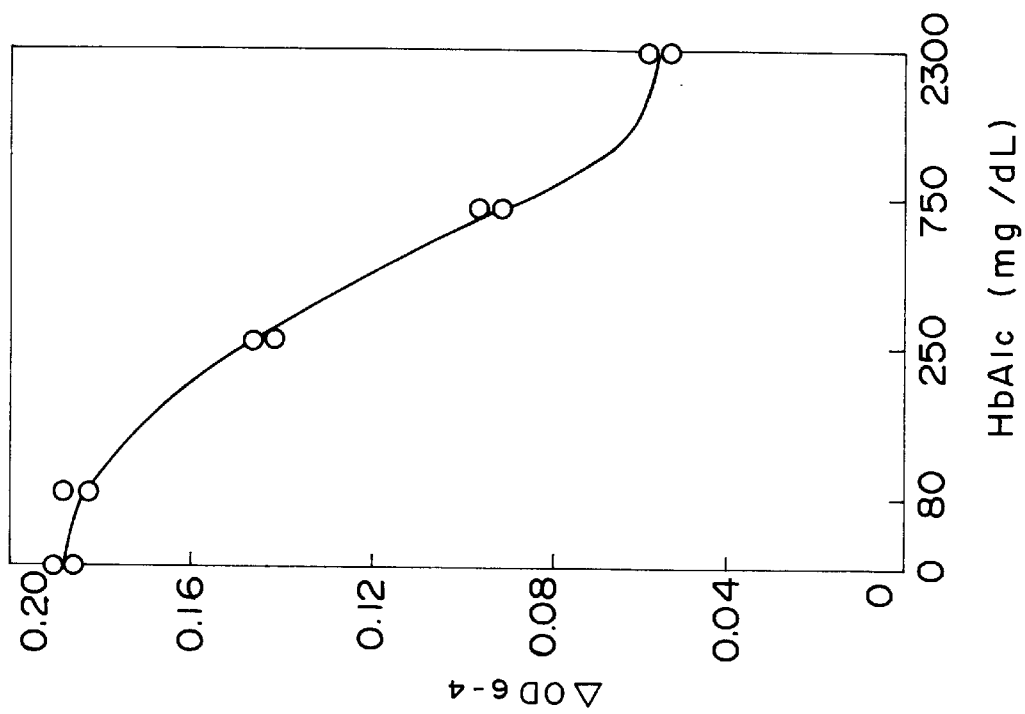

ANALYSIS ELEMENT AND METHOD FOR ANALYZING GLYCATED HEMOGLOBIN CONTENT RATIO

BACKGROUND OF THE INVENTION

1. Field of the Invention

The present invention relates to an analysis element for measuring glycated hemoglobin ($HbA_1$, also referred to as hemoglobin $A_1$) content ratio, by which amount of glycated hemoglobin and total hemoglobin are simultaneously and separately analyzed and the glycated hemoglobin ratio is calculated. The present invention also relates to an analysis method of glycated hemoglobin content ratio using this element. Particularly, the present invention relates to an analytical element for measuring the glycosylation level of hemoglobin by analyzing the amount of hemoglobin $A_{1c}$, which is one of classes of glycated hemoglobins, and total hemoglobin simultaneously and the glycosylation level of hemoglobin is calculated, and relates to the analysis method of the glycosylation level of hemoglobin using this element.

2. Description of the Related Art

Hemoglobin (Hb) is a respiratory pigment present in erythrocyte, which is largely responsible for oxygen transport. A hemoglobin molecule comprises four polypeptide subunits (respectively two α chain systems and β chain systems), each subunit is formed by association of one globin protein and one heme molecule which is an iron-protoporphyrin complex. Major class of hemoglobin (more than 90%) found in normal adult hemolysate is adult hemoglobin (HbA: also referred to $HbA_0$ for distinguishing from glycated hemoglobin $HbA_1$ described hereinafter) having $\alpha_2\beta_2$ subunits composition; and trace components such as $HbA_2$ ($\alpha_2\delta_2$) are also found in normal adult.

Among classes of adult hemoglobin HbAs, there is known a glycated hemoglobin (HbA1, also referred to as glycosylated hemoglobin), which may be further classified fractionated into $HbA_{1a1}$, $HbA_{1a2}$, $HbA_{1b}$, and $HbA_{1c}$ with an ion exchange resin fractionation. All of these subclasses have the same primary structure, which is stabilized by formation of an aldimine (Schiff base) by the amino group of N-terminal valine in β subunit chain of normal hemoglobin HbA and glucose (or, glucose-6-phosphate or fructose) followed by formation of ketoamine by Amadori rearrangement.

In particular, glycated hemoglobin bound with glucose is called $HbA_{1c}$ (glycosylated hemoglobin, hereinafter also referred to as hemoglobin $A_{1c}$), and comprises main portion of glycated hemoglobins. The content ratio of glycosylated hemoglobin is proportional to blood glucose level, and ranges 3–6% in total hemoglobin Hb of normal human adult, though it can go up to 15% in that of diabetics. Hence, determination of the amount of glycosylated hemoglobin $HbA_{1c}$ is considered to be a good index for carbohydrate metabolism control. In addition, since ketoamine formed by a non-enzymatic reaction with blood glucose is stable, this glycosylated hemoglobin $HbA_{1c}$ is never decomposed during the life of erythrocyte (120 days in average). Thus, the amount of hemoglobin $A_{1c}$ in blood is understood to memorize blood glucose levels of last 1 or 2 months. Accordingly, blood glucose levels of the last two months or so can be estimated on the basis of the ratio of $HbA_{1c}$ to total hemoglobin Hb. Analysis of the hemoglobin $A_{1c}$ in blood is used as a measurement enabling long-term control of blood glucose level, whereas blood glucose level which goes up for a temporary short period after eating is used as an index of a short-term blood glucose level.

Although a hemoglobin $A_{1c}$ analysis has been conventionally performed by column chromatography using HPLC (high pressurized liquid chromatography) or mini columns, the column method not only requires an expensive measuring apparatus for exclusive use, but also takes time for the analysis, and thus was not suitable for clinical examinations in which a number of specimens are to be handled.

In recent years, $HbA_{1c}$ analyses by a turbidimetric immunoassay method or ELISA (enzyme labelled immunosorbent assay) have been proposed (e.g. Unexamined Japanese Patent Publication Nos. 277967/1988 and 46566/1991). However, measurement operation of prior art is complicated, and the analysis requires skill. In addition, there is inconvenient in that the total hemoglobin Hb amount has to be measured by another method although the $HbA_{1c}$ content ratio is possible to be analyzed by the above mentioned method. Similar problems are also raised in the analyses of glycated hemoglobins other than $HbA_{1c}$. Hence, there is a demand for more simple and rapid method for analyzing the ratio of $HbA_{1c}$ or other glycated hemoglobin to total hemoglobin with high sensitivity.

SUMMARY OF THE INVENTION

The present invention has been accomplished in view of the aforementioned circumstances, and a first object of the present invention is to provide an analysis element for analyzing a glycated hemoglobin content ratio, which enables a simultaneous analysis of both glycated hemoglobin such as hemoglobin $A_{1c}$ and total hemoglobin Hb for calculation of the glycated hemoglobin content ratio, with simple and rapid operation at a high sensitivity.

A second object of the present invention is to provide a process for analyzing a glycated hemoglobin content ratio using the aforementioned analytical element.

The first object of the present invention is achieved by the provision of an analysis element for analyzing both amounts of glycated hemoglobin and total hemoglobin in an aqueous liquid sample so as to calculate glycated hemoglobin content ratio in the sample, the element comprising:

a substrate layer for receiving a reaction mixture after the completion of an immunological reaction between the glycated hemoglobin in the sample and an enzyme-labelled antibody against the glycated hemoglobin, said substrate layer containing a non-diffusible substrate which forms a diffusible material in the presence of the enzyme of said enzyme-labelled antibody, the activity of said enzyme being effected relative to the steric hindrance due to said immunological reaction; and a reagent layer containing a reagent composition for reacting with the diffusible material to form a dye which is detectable colorimetrically in a wavelength range which is not effected by an absorption spectrum of the hemoglobin;

whereby the total hemoglobin retained in said substrate layer and the dye formed in said reagent layer are able to be colorimetrically analyzed separately.

In a principle, the analysis element of the present invention enables a simultaneous, separate measurement of the amount of glycated hemoglobin ($HbA_1$) and total hemoglobin in the sample by measuring the formed dye corresponding to glycated hemoglobin and the color inherent in hemoglobin in a different wavelength range, and simplifies calculation of glycated hemoglobin content ratio ($HbA_1$/total-Hb). In the case of measuring glycosylated hemoglobin ($HbA_{1c}$) as glycated hemoglobin, the determined content ratio ($HbA_{1c}$/total-Hb) is the glycosylation level of hemoglobin.

In a preferred embodiment, a fragmenting enzyme for further fragmenting the diffusible material may be contained in the reagent layer or a layer underlying below the reagent layer so that the fragmented product having a lower molecular weight is detected with an appropriate color-developing reagent composition. In a modified embodiment, the enzyme-labelled antibody may be previously contained in the substrate layer or another layer laminated on the substrate layer.

When the substrate of labelling enzyme is a non-diffusible substrate which forms a diffusible material susceptible of colorimetry in a wavelength range different from and non-overlapped with main absorption wavelength range of hemoglobin, the detection layer instead of the reagent layer may be provided so that the diffusible material (dyestuff or pigment) can be detected in this detection layer.

The second object of the present invention is achieved by an analysis method for analyzing both amounts of glycated hemoglobin and total hemoglobin in an aqueous liquid sample so as to calculate glycated hemoglobin content ratio in the sample, the method comprising the steps of:

(a) mixing the aqueous liquid sample containing hemoglobin including glycated hemoglobin with an enzyme-labelled antibody against the glycated hemoglobin to allow the antigen-antibody reaction between the glycated hemoglobin and the enzyme-labelled antibody;

(b) supplying the reaction mixture after the completion of said antigen-antibody reaction to a substrate layer containing a non-diffusible substrate which forms a diffusible material in the presence of the enzyme of said enzyme-labelled antibody, the activity of said enzyme being effected relative to the steric hindrance due to said antigen-antibody reaction;

(c) allowing said diffusible material formed in said substrate layer to migrate to a reagent layer which contains a reagent composition for reacting with the diffusible material to form a dye, the formed dye being detectable colorimetrically in a wavelength range which is not affected by an absorption spectrum of the hemoglobin;

(d) measuring colorimetrically the amount of the formed dye in the reagent layer to analyze quantitatively the glycated hemoglobin contained in the sample;

(e) measuring the amounts of the total hemoglobin retained in the substrate layer and its upper layer by the colorimetrical determination at a wavelength range in which the hemoglobin has its inherent absorption, to analyze quantitatively the total hemoglobin content ratio in the sample; and (f) calculating the ratio of the obtained glycated hemoglobin amount to the total hemoglobin amount so as to determine the glycated hemoglobin content ratio in the sample.

Where the substrate of labelling enzyme is a non-diffusible substrate which forms a diffusible material detectable colorimetrically in a wavelength range different from and non-overlapped with main absorption wavelength range of hemoglobin, it is possible to allow this diffusible material (dyestuff or pigment) to migrate to the detection layer instead of the reagent layer so that the diffusible material can be detected therein. The glycated hemoglobin content ratio ($HbA_1$/total-Hb) can be calculated on the basis of the ratio of the obtained amount of glycated hemoglobin ($HbA_1$) to the amount of total hemoglobin, the total hemoglobin amount (concentration) in the sample solution (specimen) being analyzed colorimetrically in the hemoglobin-specific absorption wavelength range.

The enzymatic activity of the enzyme of the enzyme-labelled antibody, which is bound to glycated hemoglobin ($HbA_1$), towards the non-diffusible substrate is interfered or effected by steric hindrance. As a result, the quantity of the diffusible material formed in the substrate layer is in inverse proportion to the quantity of the antigen ($HbA_1$) contained in the sample. The reaction product formed in the substrate layer rapidly migrates into the reagent layer and may be detected in the reagent layer. The unreacted non-diffusible substrate is held in the substrate layer.

By the reaction with the color reagent composition in the reagent layer, the diffusible material forms a coloring dye having a detectable absorption spectrum which is different from or non-effected by the absorption spectrum of hemoglobin within measurement wavelength range. In other words, the formed dye may be measured within wavelength range which is not effected by the absorption spectrum of the hemoglobin. Consequently, the amount (concentration) of glycated hemoglobin may be measured on the basis of the amount of formed dye. On the other hand, the total amount of hemoglobin can be measured separately from the formed dye derived from the glycated hemoglobin analysis, if a wavelength (e.g. 540 nm) is selected appropriately for the main absorption wavelength of the total hemoglobin. Hemoglobin has a much greater absorption peak also around 400 nm in addition to the absorption peak at 540 nm. When total hemoglobin concentration in the sample solution is high to a certain extent, it is convenient to choose the absorption peak at 540 nm as its main absorption wavelength for measurement of hemoglobin. However, when total hemoglobin concentration in the sample solution is low to a certain extent (e.g. when a whole blood sample is highly diluted), the absorption peak at 540 nm might be too low to obtain quantitative accuracy in some cases. In latter case, it is convenient to choose the absorption peak at 400 nm as the main absorption wavelength for measuring the total amount of hemoglobin.

Other hemoglobin classes such as $HbA_0$, $HbA_2$ etc. can not recognize and bind to the antibody against glycated hemoglobin such as $HbA_{1c}$. Any of these other hemoglobin classes has also a high molecular weight. Therefore, the diffusion of other hemoglobin classes to the reagent layer is much slower than the diffusible reaction product. As a result, the remaining other hemoglobin classes which are free and have not bound with the antigen is retained in the substrate layer, together with $HbA_1$-antibody complex. Preferably, the diffusion resistance of the reagent layer may be varied in relative to that of the substrate layer. For example, the lower reagent layer may be composed of a non-porous medium (e.g. a hydrophilic binder layer) having relatively large diffusion resistance and the upper substrate layer may be composed of a porous medium having small diffusion resistance. With such layer construction, high molecular weight proteins including hemoglobins remain on the interface between the reagent layer and the substrate layer so that total hemoglobin may be detected on this interface with high accuracy.

From the measured values of $HbA_1$ and total hemoglobin (Hb), the glycated hemoglobin content ratio (%) can be calculated according to the following equation.

$$(HbA_1/Hb) \times 100 \ (\%)$$

When the amount of glycosylated hemoglobin ($HbA_{1c}$) is measured as $HbA_1$, the calculated content ratio indicates the glycosylation level of hemoglobin.

When the lower slopes trailing from the peak of the absorption spectrum pattern of the formed dye overlap with the major peak of the absorption spectrum of hemoglobin, absorbancy at the measurement wavelength for measuring the total amount of hemoglobin varies or increases due to color of the formed dye. This raises an error. In this case, the fact may be utilized that color development of the formed dye requires a certain period of time during which the diffusible material (dye precursor) migrates from the reagent layer to the substrate layer and takes place coloring reaction within the substrate layers. It should be noted that there is time lag until diffusible material formed in the substrate layer transports to the reagent layer and develops color therein. In contrast, the total hemoglobin amount can be measured shortly after spotting the sample onto the element. By using such phenomena in the layer structure, the colorimetrical measurement of total hemoglobin may be conducted before the dye is formed or developed, and in later colorimetrical measurement of the formed dye after the color develops may be conducted. Such differential or time-interval colorimetrical measurements may realize to prevent the error of total hemoglobin measurement.

BRIEF DESCRIPTION OF THE DRAWINGS

FIG. 4 is a graphic representation showing the calibration curve when the analysis element for measuring glycated hemoglobin content ratio in Example 1 is used, the antigen-antibody reaction taking place in a solution system and the enzymatic reaction only taking place in the element;

FIG. 5 is a graphic representation showing the calibration curve when the analysis element for measuring glycated hemoglobin content ratio in Example 2 is used, both of immunological reaction and enzymatic reaction taking place in the element and the sample being a human $HbA_{1c}$ solution;

DESCRIPTION OF THE PREFERRED EMBODIMENTS

Layer Construction of Immunoassay Element

Figure 1:
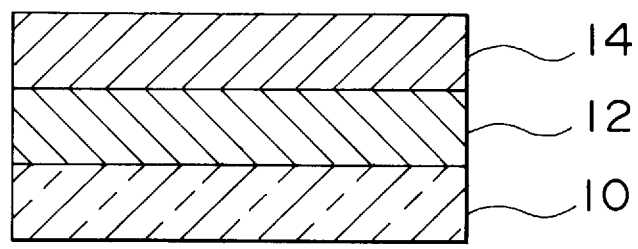
FIG. 1 is an illustration showing the principal layer structure of one embodiment of the analysis element for analyzing glycated hemoglobin content ratio according to the present invention.

FIG. 1 shows an embodiment of the immunoassay element according to this invention.

In this Figure, reference numeral 10 designates a transparent support on which laminated are reagent layer 12 and a substrate layer 14. The substrate layer 14 is composed of a water-permeable material and contains a non-diffusible substrate for a labelling enzyme which forms a conjugate with the anti-$HbA_1$ antibody. The reagent layer 12 is composed of a water-permeable material and contains a reagent composition for detecting the diffusible material which has been diffused or migrated from the substrate layer.

In a preferred embodiment, the reagent layer 12 further contains a fragmenting enzyme for further fragmenting the diffusible material into a lower molecular weight product, so that the reagent composition detects thus formed lower molecular weight product.

When the diffusible product of the enzymatic reaction is a material which may be detected directly, such as a colored material, the layer 12 need not contain any reagent composition and thus layer 12 serves as a detection layer. In such case, the diffusible material preferably has an absorption wavelength spectrum which can be separately detected from hemoglobin; thereby, glycated hemoglobin ($HbA_1$) and total hemoglobin (Hb) may be analyzed separately and simultaneously.

In this principle structure of the immunoassay element of the present invention, the antigen-antibody binding reaction is effected only between the analyte and the enzyme-labelled antibody, and the reaction mixture is spotted on or supplied to the substrate layer 14. In this case, the amount of the diffusible material formed in the substrate layer is decreased as the amount of $HbA_1$ (the antigen to be analyzed) is large.

Analyte (Substances to be analyzed)

The substance to be analyzed by the present invention (hereinafter simply referred to as "analyte") is the glycated hemoglobin ($HbA_1$), preferably human glycosylated hemoglobin ($HbA_{1c}$), contained in the sample. The sample containing the analyte is most preferably prepared by adding a diluent to the blood collected from an examinee such as a diabetes patient. The diluent may be a buffer solution as well as purified water. The sample to be analyzed is needed to be subjected to the complete hemolysis so as to fully solubilize the hemoglobin into the solution. A commercially available hemolysis agent or surfactant (for example, Triton X-100) may be used for this purpose. Alternatively, the hemolysis may be done by osmotic shock using a non-isotonic diluent. If required, erythrocyte membrane may be subjected to ultrasonic disintegration. The hemolysis may be done by freezing and melting. Before specimen assay, the sample is prepared by suitable dilution with a diluent.

Examples of the surfactant which may be used for the hemolysis agent include: anionic surfactants such as sodium dodecyl sulfate (SDS) and dioctyl sodium sulfosuccinate (DONS), as described in Unexamined Japanese Patent Publication No. 11510/1994 (corresponding to DE 4206932A); cationic surfactants such as tetradecyl trimethylammonium bromide (TTAB) and cetyl trimethylammonium bromide (CTAB); and ampholytic surfactants such as caboxybetaine types. Nonionic surfactants may be also used such as alkylphenoxy-polyethoxy ethanol (for example, Triton X-100) and alkylphenoxy polyglycidol (for example, Surfactant 10G).

Antibody

The antibody labelled with an enzyme, to be used, is a specific antibody for the analyte glycated hemoglobin ($HbA_1$). Although a polyclonal antibody (antiserum) may be used, use of a monoclonal antibody improves the sensitivity further. The monoclonal antibody may be a fragment such as $F(ab')_2$, Fab' and Fab. Some of the specific antibodies might have a slight cross-reactivity with hemoglobin which is not glycosylated (non-glycosylated Hb). When such specific antibody is used, the ratio of cross-reaction with total hemoglobin (normally, total hemoglobin obtained from whole blood of normal human) is to be determined preliminarily; thereby, the error (increment) in $HbA_1$ assay value caused by the cross reaction is calculated. True $HbA_1$ value is obtained by subtracting the error from the assayed $HbA_{1c}$ value.

Labelling Enzyme

The enzyme for forming the enzyme-antibody conjugate may be selected in consideration of the combination of the substrate which is used at the subsequent enzymatic reaction. Since the reactivity to the enzyme which reacts with the substrate is suppressed by the steric hindrance by the presence of the matrix structure formed by the enzyme, the antigen and the antibody according to the present invention, it is preferable that the combination of the enzyme and the substrate is selected so that the influence by the steric hindrance is easily detected. It is thus preferred to attain a higher sensitivity that a substrate having a relatively large molecular weight is selected. A substrate having a molecular weight of not less than about 20,000 daltons preferably not less than about 100,000 daltons is used in the invention. Examples of such substrates include starch as the substrate for enzyme amylase; substrate cellulose as the substrate for enzyme cellulose; proteins such as gelatin and hemocyanin as the substrate to protease; and various oils and fats as the substrate for lipase. Detailed reports relating to the selection of the enzymes and substrates are disclosed in Unexamined Japanese Patent Publication Nos. 108756/1985 (corresponding to EP 0144176A and U.S. Pat. No. 4,692,404), 171461/1985 (corresponding to EP 0152305A and U.S. Pat. No. 4,757,001) and 171460/1985 (corresponding to EP 0152305A and U.S. Pat. No. 4,757,001). Amylase used with starch as the substrate is preferred. It is particularly preferred that the substrate is a water-insoluble substrate, since the steric hindrance by the presence of the enzyme-antibody-antigen matrix structure is noticeably appeared.

Usable amylases include α-amylase, β-amylase and glucoamylase, and it is preferable for the prevention of noise to use an amylase which is not substantially contained in the sample. These amylases are contained in various resources including animals (saliva, pancreatic juice, etc.), plants and bacteria. When a body fluid or blood of human being or an animal is analyzed, it is preferable that the use of an amylase originated from a higher animal is obviated.

Examples of amylase originated from bacteria or plants include glucoamylases originated from Aspergillus, Rhizopus or Saccharomyces; β-amylases originated from malt of barley, wheat and soybean; and α-amylases originated from Bacillus subtilis, Streptomyces griseus, Pseudomonas stutzeri and Thermoactiomyces vulgaris. The most preferable amylase is the α-amylase originated from Bacillus subtilis, because it is excellent in liquefying power and resistance to heat.

It is preferable that the enzyme is not affected by any hindering factor present in the sample, and that competitive homologous enzymes are not present in the sample. However, if an enzyme homologous to the labelling enzyme is present in the sample, an enzyme inhibitor may be used. It suffices that the used enzyme inhibitor inhibits activity of the enzyme contained in the sample to a greater extent than the inhibiting activity of the labelling enzyme. Most preferably, the used enzyme inhibitor inactivates the enzyme in the sample completely and does not deactivate the labelling enzyme. However, in practice, it suffices that the blank value at the measuring step is not raised by the use of the enzyme inhibitor, the restoration of the activity of the enzyme contained in the sample after the measuring step, which might be caused by deactivation of the used enzyme inhibitor, being allowable. It is allowable that the enzyme inhibitor inhibits the activity of free enzyme as far as it does not inhibit the enzyme in the enzyme-labelled antibody. An enzyme inhibitor having the specific characteristics as described above may be selected from known enzyme inhibitors and used in the invention. Alternatively, an antibody against the enzyme which is contained in a sample to cause a problem is prepared and the antibody thus prepared is used as an enzyme inhibitor.

When an α-amylase is used as the enzyme, carboxymethylated starch, starch, amylose, amylopectin or the like may be used as the substrate. It is particularly preferred for the improvement in sensitivity to use water-insoluble starch, since the enzymatic reaction takes place on the surfaces of the substrate particles, namely the reaction takes place at the solid-liquid interface to exaggerate the influence of steric hindrance to the enzymatic activity by the occurrence of antigen-antibody binding. Alternatively, a water-insoluble dye-starch may be used, followed by detection of the dye bound to the soluble amylose which is the decomposition product of enzymatic reaction. An example of commercially available water-insoluble blue starch polymer is Neo Amylase (produced by Dai-ich Pure Chemicals, Co., Ltd.).

Linking between Enzyme and Antibody

The enzyme may be linked to the antibody while utilizing the functional groups (amino, carboxyl, thiol, etc.) of the enzyme and the antibody. Representative linking methods include the glutaraldehyde method, the periodic acid method, the pyridyl-disulfide method, and the maleimide-succinimide method. The linking method is not limited only to the representative methods as described above, and may be selected from the methods described in "Method in Immunology and Immunochemistry", vol. 1, (C. A. Williams, M. W. Chase, Academic Press (1967)) or "KOSO MEN'EKI SOKUTEI-HO (Enzyme Immunoassay), edited by Ishikawa, Kawai and Miyai, Igaku Shoin, 1978. The maleimide-succinimide method, in which thiol group at the hinge region of the antibody is linked with amino group of the enzyme, is preferred since it is excellent in reaction efficiency while retaining the activity of the antibody.

In the maleimide-succinimide method, the enzyme is linked with Fab', for example, through the following steps. Initially, amino groups of the enzyme are maleimidated by the maleimide-succinimide reagent. The reaction product is subjected to gel filtration for purification, and then subjected to the reaction for forming a conjugate with antibody (Fab') having thiol groups. It is preferable that the molar ratio of the enzyme to the antibody in the conjugate forming reaction ranges from 1:3 to 1:7. For example, when a Fab' (having a molecular weight of about 50,000) is used as the antibody and an α-amylase (having a molecular weight of about 50,000) is used as the enzyme, the preferable weight ratio of the α-amylase to the weight of the Fab' ranges from ⅓ to ⅐. This linking reaction proceeds generally at 4° C. to room temperature.

The enzyme-antibody complex (enzyme-labelled antibody) thus prepared is purified through gel filtration, and dried through lyophilization as desired. The ratio between the enzyme and the antibody in the linked product is not limited to 1:1, but may be changed to a desired ratio in consideration of the applied use of the product. In general, since the enzyme has plural amino groups, plural maleimide groups are introduced and linked with plural antibody molecules. The molar ratio of antibodies to the enzyme in the produced complex preferably ranges from 4 to 5 in order to ensure high detection sensitivity. When Fab' fragment (having a molecular weight of about 50,000) is used as the antibody and an α-amylase (having a molecular weight of about 50,000) is used as the enzyme, the preferable molecular weight of the enzyme-antibody complex ranges from 150,000 daltons, more preferable from 250,000 to 300,000 daltons, to ensure high detection sensitivity.

Layer Structure of the Analysis Element

The dry immunoassay element of this invention may have a layer structure similar to those of various dry analysis elements. The element may be of a multi-layered construction including, in addition to the substrate layer and the reagent layer, a support, a spreading layer, a detection layer, a light-shielding layer, an adhesive layer, a water-absorbing layer, an undercoating layer and so on. Examples of such analysis elements are disclosed in the specifications of Unexamined Japanese Patent Publication Nos. 53888/1974 (corresponding to U.S. Pat. No. 3,992,158), 40191/1976 (corresponding to U.S. Pat. No. 4,042,335), 164356/1980 (corresponding to U.S. Pat. No. 4,292,272) and 4959/1986 (corresponding to U.S. Pat. No. 5,019,347 and European Patent Publication No. 0166365A).

When a light-transmitting and water-impermeable support is used, the dry immunoassay element having the following construction may be used, although the present invention is not limited to the following constructions.
(1) A reagent layer disposed on a support, and a substrate layer superposed on the reagent layer;
(2) A reagent layer disposed on a support, an adhesive layer superposed on the reagent layer and a substrate layer superposed on the adhesive layer in this order;
(3) A support, and a detection layer, a reagent layer and a substrate layer superposed in this order;
(4) A support, and a detection layer, a reagent layer, adhesive layer and a substrate layer superposed in this order.

In the constructions (1) to (4), the reagent layer may be composed of plural layers. The reagent layer may be an immunological reaction layer which contains a component (an enzyme-labelled antibody), capable of taking part in an immunological reaction, as will be described hereinafter.

A water-absorbing layer may be disposed between the support and the reagent or detection layer. Filtering layers may be interposed between the adjacent layers. A spreading layer may be disposed on the substrate layer, or the substrate layer may serve also as a spreading layer. When the total hemoglobin content in the substrate layer is to be detected from the upper layer (opposite side from the support), installation of a light-reflection layer or a light-shielding layer under the substrate layer is preferred.

Substrate Layer

The substrate layer 14 is composed of a water-permeable layer and contains a non-diffusible substrate which is a substrate for the enzyme labelling the anti-HbA$_1$ antibody. In order to ensure water-permeability of the substrate layer, it is preferable that the substrate layer is composed a porous medium or a layer composed of a hydrophilic polymer binder.

The porous layer may be fibrous or non-fibrous. As the fibrous material, filter paper, non-woven cloth, woven cloth (e.g. plain woven cloth), knitted cloth (e.g. tricot knitted cloth) or filter paper made of glass fibers may be used. Examples of the non-fibrous material include a membrane filter composed of cellulose acetate described in Unexamined Japanese Patent Publication No. 53888/1974 (corresponding to U.S. Pat. No. 3,992,258), and a particulate structure layer containing interconnected voids and composed of inorganic or organic fine particles as disclosed in Unexamined Japanese Patent Publication Nos. 58333/1974 (corresponding to U.S. Pat. No. 3,992,258), 90859/1980 (corresponding to U.S. Pat. No. 4,258,001) and 70163/1983 (corresponding to U.S. Pat. No. 4,486,537). A laminated structure made of partially bonded multiple porous layers may also be preferably used, examples of such structure being disclosed in Unexamined Japanese Patent Publication Nos. 4959/1986 (corresponding to U.S. Pat. No. 5,019,347 and EP 0166365A), 116258/1987 (Chemical Abstracts, 108, (1988):3041y), 138756/1987 (EP 0226465A), 138757/1987 (EP 0226465A) and 138758/1987 (EP0226465A).

The porous layer may be a spreading layer having a so-called metering function to spread a liquid over an area substantially in proportion to the volume of the liquid fed thereto. Preferable materials for the spreading layer are woven and knitted fabrics. The woven fabrics or like may be subjected to the glow discharge treatment as described in Unexamined Japanese Patent Publication No. 66359/1982 (corresponding to GB 2,087,974A and U.S. Pat. No. 4,783, 315). In order to adjust the area or rate for spreading, the spreading layer may contain a hydrophilic polymer or a surfactant as described in Unexamined Japanese Patent Publication Nos. 222770/1985 (corresponding to EP 0162301A), 219397/1988 (corresponding to DE 37 17 913A), 112999/1988 (corresponding to DE 37 17 913A), and 182652/1987 (corresponding to DE 37 17 913A).

One convenient method for introducing the substrate in the substrate layer is a method wherein the substrate is impregnated into or coated on a porous membrane made of, for example, paper, cloth or a high polymer, and then the composite is applied on another water-permeable layer, for example, a reagent layer superposed on the support by a method as described in Unexamined Japanese Patent Publication No. 164356/1980 (corresponding to U.S. Pat. No. 4,292,272). A further method comprises the steps of bonding a porous layer on another water-permeable layer (for example a reagent layer) by a method as described above, and coating a composition containing the substrate on the porous layer. Any known methods may be employed for the impregnation or coating on the porous layer. Coating may be effected by selecting a suitable method, for example, dip coating, doctor coating, hopper coating and curtain coating.

Although the thickness of the substrate layer 14 made by any of the aforementioned methods is not limited, the thickness may range within 1 μm to 50 μm, and preferably, from 2 μm to 30 μm, when the layer is provided as a coating layer. When it is provided by another method, for example by piling of a laminate, the thickness thereof may be varied within a wide range of from several tens of μm to several hundreds of μm.

The substrate layer 14 may be a water-permeable layer composed of a hydrophilic polymer binder, such as, gelatin and derivatives thereof (e.g. phthalated gelatin), derivatives of cellulose (e.g. hydroxyethyl cellulose), agarose, sodium alginate, acrylamide copolymers, methacrylamide copolymers, copolymers of acryl amides or methacrylamides with various vinyl monomers, polyhydroxyethyl methacrylate, polyvinyl alcohol, polyvinyl pyrrolidone, sodium polyacrylate, and copolymers of acrylic acid with various vinyl monomers.

The substrate layer composed of a hydrophilic polymer binder may be provided by coating an aqueous solution or dispersion of the substrate, an additional other reagent composition and a hydrophilic polymer binder on another layer, such as a support or a detection layer, and then drying the coated solution or dispersion, as disclosed in the specifications of Japanese Patent Publication No. 21677/1978 (corresponding to U.S. Pat. No. 3,992,158), Unexamined Japanese Patent Publication Nos. 164356/1980 (corresponding to U.S. Pat. No. 4,292,272), 101398/1979 (corresponding to U.S. Pat. No. 4,132,528), and 292063/1986 (Chemical Abstracts, 106, (1987): 210567y). The thickness of the dried substrate layer containing a hydrophilic polymer as the binder may range from about 2 μm to about 50 μm, and preferably, from about 4 μm to about 30 μm, and the coverage thereof may range from about 2 g/m$^2$ to about 50 g/m$^2$, and preferably, from about 4 g/m$^2$ to about 30 g/m$^2$.

To improve the characteristics, such as, coating characteristics, diffusibility of the diffusible material, reactivity and storage stability, the substrate layer 14 may include, in addition to the non-diffusible substrate, various organic or inorganic additives, for example, enzyme activators, coenzymes, surfactants, pH buffer reagents, fine particles, antioxidants, etc. Examples of buffer system, which may be contained in the substrate layer, include pH buffer reagents as described in "KAGAKU BINRAN, KISOHEN" edited by Japanese Chemical Society (MARUZEN, Tokyo. 1966), pp1312–1320; R. M. C. Dawson et al., "Data for Biological Research", 2nd Edition (Oxford at the Clarendon Press, 1969), pp476–508; "Biochemistry", 5, pp467–477 (1966); and "Analytical Biochemistry", 104, pp300–310 (1980). Specific examples of usable buffers are buffer reagents containing tris (hydroxymethyl)aminomethane (Tris), buffer reagents containing phosphates, buffer solutions containing borates, buffer reagents containing citric acid or citrates, buffer reagents containing glycine, buffer solutions containing Bicine, and buffer reagents containing HEPES.

Reagent Layer

The reagent layer 12 contains a reagent composition for detecting the diffusible material which has diffused and migrated from the substrate layer 14. As desired, a fragmenting enzyme may be contained in the reagent composition and a detection reagent composition for detecting the lower molecular weight product formed by the action of the fragmenting enzyme may also be contained.

The reagent layer 12 is composed of a water-permeable layer which is preferably a continuous layer made of a hydrophilic polymer binder, similar to the water-permeable layers as described in the description of the substrate layer. The used hydrophilic polymer binder may be determined in consideration of the diffusible product formed in the substrate layer and the coloring reagent contained in the reagent layer.

It is preferable that the reagent layer 12 is composed of a material selected from those in which proteinous ingredients such as hemoglobin, which has diffused and developed in the upper substrate layer, may hardly migrate from the upper substrate layer into this reagent layer. In a view of this point, it is desirable that the substrate layer 14 is composed of a porous medium having relatively low diffusion-resistance and that the reagent layer 12 is composed of a non-porous medium (for example, a hydrophilic polymer binder) having large diffusion-resistance to macromolecule substances such as protein. By such a layer construction, the free hemoglobin unbonded to the anti-glycated hemoglobin antibody will be held in the interface between the substrate layer 14 and the reagent layer 12, and will spread uniformly on the interface. Thus, the photometric surface in the intensity determination of optical reflection for the hemoglobin pigment is made smooth and flat, not in rough concave and convex, thereby the measurement accuracy is improved. The hemoglobin which has reached the interface in this way undergoes smaller oxidation and denaturation and is less susceptible to drying, in comparison with the case where the hemoglobin is located and still remains on or at the sample-spotted surface of the uppermost layer of the element. Hence, the measured values do not fluctuate and are very stabilized in the total hemoglobin determination, and the measurement accuracy is improved.

When the diffusible material diffused and migrated from the substrate layer 14 is a material which can be directly detected, the layer 12 needs not contain any detection reagent composition so that the layer 12 serves as a detection layer. When the layer 12 is a detection layer, it is desirous that the layer 12 is composed of a continuous layer composed of a hydrophilic polymer binder selected from the water-permeable layers as described hereinbefore in the description relating to the substrate layer.

Support

The support 10 may be light-nontransmitting (opaque), light-semi-transmitting (translucent) or light-transmitting (transparent), and it is generally preferable that the support is light-transmitting and water-impermeable. Preferable materials for the light-transmitting and water-impermeable support are polyethylene terephthalate and polystyrene. In general, an undercoating is provided or the support is subjected to hydrophilization treatment in order to firmly adhere the hydrophilic layer.

Immunological Reaction Layer

The substrate layer 14 shown in FIG. 1 may contain enzyme-labelled antibody, in addition to the non-diffusible substrate, to form an immunological reaction layer in which an immunological reaction takes place. With such a construction, a homogeneous enzyme immunological reaction takes place in the element only by spotting a sample on the element.

Figure 2:
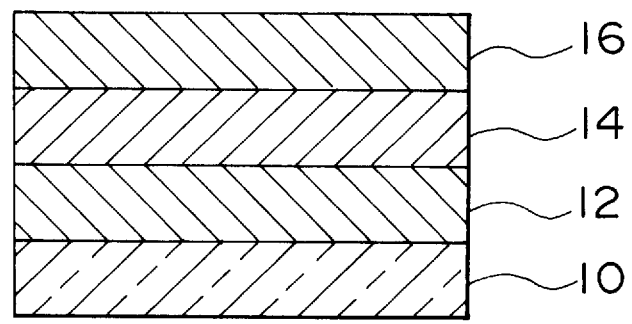
FIG. 2 is an illustration showing another embodiment of the analysis element for analyzing glycated hemoglobin content ratio according to the present invention.

Alternatively, the enzyme-labelled antibody may be contained in separate a layer other than the substrate layer. For example, as shown in FIG. 2, the immunoassay element may comprise a water-permeable layer 16 containing the enzyme-labelled antibody and superposed on the substrate layer 14. With such a construction, hemoglobin HbA$_{1c}$, in the sample binds with the antibody of the enzyme-labelled antibody contained in the layer 16, and then migrates into the substrate layer 14.

In order to contain an enzyme-labelled antibody in a separate layer in the substantially dry state or in the substantial absence of water, the enzyme-labelled antibody may be dissolved or dispersed in a non-aqueous medium, such as an alcohol (e.g. ethanol) and then the solution or dispersion is impregnated in the water-permeable layer.

Labelling Enzyme/Non-Diffusible Substrate/
Fragmenting Enzyme

In the dry immunoassay element of the invention, the sensitivity can be improved by adding a fragmenting enzyme for further fragmenting the diffusible material, which is the decomposed product of the non-diffusible substrate by the labelling enzyme, to a lower molecular weight material to the reagent layer 12, in the same manner as described in Unexamined Japanese Patent Publication Nos. 295466/1991 (corresponding to EP 0451848A), 128655/1992 and 276551/1992 (corresponding to EP 0503459A). The combination of the labelling enzyme and the fragmenting enzyme may be selected so that the labelling enzyme reacts with the non-diffusible substrate to form a diffusible material which is further fragmented by the fragmenting enzyme to form a lower molecular weight product which can be easily detected.

In detail, the labelling enzyme of the enzyme-labelled antibody is selected so that it decomposes the non-diffusible polymer substrate to form a diffusible product which can be further fragmented by the fragmenting enzyme to form a lower molecular weight product. The non-diffusible substrate is selected so that the substrate per se is non-diffusible (insoluble) in the aqueous sample liquid and thus does not diffuse or migrate from the immunological reaction layer 14 to the reagent layer 12. The fragmenting enzyme is selected so that it fragments the diffusible substance or material produced from the non-diffusible substrate under the action of the labelling enzyme to produce a lower molecular weight product which is easily detected. Specific examples of the labelling enzyme, non-diffusible substrate and fragmenting enzyme will be described below.

Labelling Enzyme

Examples of suitable enzyme include hydrolase which forms diffusible oligomers from non-diffusible substrate composed of polymers. Among the labelling enzymes described hereinbefore, glucosidase is preferred. Examples of glucosidase are α-amylase, β-amylase, glucoamylase and lysozyme.

Non-Diffusible Substrate

Examples of the substrate for said α-amylase, β-amylase and glucoamylase are carboxymethylated starch and starch. When carboxymethylated starch or starch is used as the non-diffusible substrate, α-amylase may be used as the labelling enzyme, and glucoamylase or α-glucosidase may be combined as the fragmenting enzyme as will be described hereinafter.

Fragmenting Enzyme

The fragmenting enzyme may be an enzyme of the same kind as of the labelling enzyme. In such a case, it is preferred that the labelling enzyme is an endo-active enzyme which fragments or digests the molecule intramoleculary to produce an oligmer, and that the fragmenting enzyme has an exo-activity to act the molecule at the terminal thereof to produce a monomer. For instance, when the non-diffusible substrate is a polymer (e.g. starch), a fragmenting enzyme for decomposing the diffusible oligomer (e.g. maltose) produced by the action of the labelling enzyme to a monomer (e.g. glucose) is used. Examples of the fragmenting enzyme include hydrolases for saccharides, specific example being α-amylase, β-amylase, glucoamylase and α-glucosidase. When carboxymethyl cellulose is used as the non-diffusible substrate and cellulase is used as the labelling enzyme, C1 enzyme may be used as the fragmenting enzyme.

The combination of the labelling enzyme, the non-diffusible substrate and the fragmenting enzyme may be selected from the enzymes and substrates described in the known publications (for example, "Enzyme Handbook" (Bunji Maruo and Nobuo Tamiya, Asakura Shoten, 1982); and "Biochemical Handbook" (Nobumasa Imura et al., Maruzen, 1984)).

The lower molecular weight product produced by fragmentation in the reagent layer by the action of the fragmenting enzyme may be optically detected by using a known detection reagent. Any known methods may be employed for detecting the final glucose which is formed by the action of the aforementioned fragmenting enzyme, the examples being a method in which hydrogen peroxide formed by the oxidation of glucose in the presence of glucose oxidase is detected (e.g. the method wherein a Trinder reagent is used, as described in Ann. Clin. Biochem., 6, 24 (1964) and J. Clin. Pathol., 22, 246 (1969); the method wherein a Trinder reagent is used, as described in Unexamined Japanese Patent Publication No. 50991/1974 (corresponding to U.S. Pat. No. 3,886,045), U.S. Pat. No. 3,992,158 and Unexamined Japanese Patent Publication No. 164356/1980 (corresponding to U.S. Pat. No. 4,292,272); the method wherein a reagent containing a triaryl-substituted imidazole leuco dye is used, as described in Unexamined Japanese Patent Publication No. 26188/1978 (corresponding to U.S. Pat. No. 4,089,747) and Unexamined Japanese Patent Publication No. 45557/1983 (Chemical Abstracts 99, (1983): 209284j); and the method wherein a reagent containing an imidazole leuco dye substituted with a diarylmonoaralkyl, as described in Unexamined Japanese Patent Publication Nos. 193352/1984 (corresponding to EP 0122641A) and 224677/1985 (corresponding to U.S. Pat. No. 4,665,023)). Other example methods are a method wherein NADH produced in the presence of glucose dehydrogenase and NAD is detected, and a method wherein glucose-6-phosphate produced in the presence of hexokinase is detected.

Amongst these detection methods, the most preferred is the method wherein glucose is oxidized in the presence of glucose oxidase to form hydrogen peroxide which is detected using peroxidase and a leuco dye because of its high detection sensitivity.

These detection reagents may be contained in the reagent layer 12 of the analysis element together with the fragmenting enzyme, or may be contained in another layer (for example, a second reagent layer or a detection layer) disposed below the reagent layer 12 to detect the produced lower molecular weight product. When a leuce dye is used, it is preferred that the dye is dispersed in the hydrophilic binder in a solution in a water-immiscible solvent in consideration of the stability of the formed dye.

Process for Preparing the Immunoassay Element

The dry immunoassay element of the invention may be prepared by any of the known processes described in the specifications of the aforequoted patents.

The analysis element of the invention may be cut into a square piece having sides each ranging from about 9 mm to about 30 mm or a disk having a substantially same area. It is preferred, in view of the preparation, packaging, shipping, storage and measuring operations, that the element be contained in a slide frame as described, for example, in Japanese Patent Publication No. 28331/1982 (corresponding to U.S. Pat. No. 4,169,751), Unexamined Japanese Utility Model Publication No. 142454/1981 (corresponding to U.S. Pat. No. 4,387,990), Unexamined Japanese Patent Publication No. 63452/1982, Unexamined Japanese Utility Model Publication No. 32350/1983 and Unexamined Japanese Patent Publication No. 501144/1983 (corresponding to International Publication WO 83/00391) for use as a slide for chemical analysis. For the convenience in some uses, it may be formed in a long tape shape which is contained in a cassette or magazine, or a small piece thereof may be applied on or contained in a card having an opening.

Analyzing Method Using the Immunoassay Element

The analysis element of the invention may be used for the quantitative analysis of analytes, glycated hemoglobin and total hemoglobin, in a sample liquid by using it through the operations described in the specifications of the aforequoted patents.

In a case that the enzyme-labelled antibody is contained in the substrate layer 14, for example, about 5 μl to about 30 μl, preferably 8 μl to 15 μl, of an aqueous liquid sample, such as a blood treated with hemolysis, is spotted or otherwise fed on the substrate layer 14. The analysis element spotted with the sample liquid is then incubated at a constant temperature of from about 20° C. to about 45° C., preferably at a constant temperature of from about 30° C. to about 40° C., for 1 to 10 minutes.

Glycated hemoglobin reacts with the enzyme labelled antibody contained in the substrate layer 14 and forms antigen-antibody matrix structure. Accordingly, the enzymatic activity of the labelling enzyme towards the non-diffusible substrate contained in the same substrate layer 14 is suppressed or inhibited. The reaction product (diffusible product) formed by the enzymatic reactivity, which is inversely proportional to the amount of glycated hemoglobin in the sample, diffuses and migrates to the reagent layer 12; and therein, coloration or change in color occurs by the detection reagent composition. The reflection optical density of the color or the change in color in the element may be measured from the light-transmitting support side, and the quantity of the glycated hemoglobin $HbA_{1c}$ contained in the sample can be determined using a preliminarily prepared calibration curve based on the principle of colorimetry. The volume of the spotted liquid sample and the time and temperature for incubation are maintained constant to improve the accuracy in quantitative analysis.

The hemoglobin ($HbA_0$ and others) other than glycated hemoglobin will not migrate to the reagent layer 12, as the glycated hemoglobin ($HbA_1$) bound with the antibody does not, and remains in the substrate layer 14 so that the remaining hemoglobin may color the substrate layer 14 to the color specific for hemoglobin. The color may be measured from the light-transmitting support side, and the quantity of the total hemoglobin (Hb) in the sample can be determined using a preliminarily prepared calibration curve based on the principle of colorimetry.

As to the wavelength band which is measured by the colorimetrical analysis for color development of the change of color due to the coloring reaction of the reagent composition used in the glycated hemoglobin analysis, it may be selected so that the measured absorption wavelength band or range is different from the absorption spectral band specific to the inherent hemoglobin color. With such construction, the glycated hemoglobin and total hemoglobin can be simultaneously measured on the same analytsis element. As for the absorption wavelength spectrum of hemoglobin, oxyhemoglobin has characteristic absorption peaks at two wavelengths of 577 nm and 540 nm, and deoxyhemoglobin has a broad and characteristic absorption peak at 555 nm. The color development by the reagent composition in the reagent layer 12 is preferably brought by a dye which has a large absorption coefficient at a wavelength range different from these wavelength ranges specific to the hemoglobin.

However, the absorption wavelength of hemoglobin to be selected for the purpose of measuring the amount of total hemoglobin is not limited to the range of 540 to 580 nm mentioned above. Hemoglobin has an extremely large absorption peak near 400 nm. With an ordinary sample solution, the absorption at this wavelength is too large and is not usable for determination of the total hemoglobin. However, if the hemoglobin content is small in the sample solution, the absorptiometry at 540 to 580 nm might be quantitatively inaccurate because the absorption intensity is too small. In such a case, the wavelength band near 400 nm might be selected as the main absorption wavelength band for measuring the total hemoglobin. Anyway, it is acceptable if the total hemoglobin is measurable in the accuracy allowing a quantitative analysis.

The measuring operation may be carried out while using the chemical analysis apparatus described in Unexamined Japanese Patent Publication Nos. 125543/1985, 220862/1985, 294367/1986 and 161867/1983 (corresponding to U.S. Pat. No. 4,424,191) to realize a quantitative analysis at a high accuracy by extremely easy operations.

When the analysis element does not contain the enzyme-labelled antibody, the aqueous sample liquid is mixed with a solution containing the enzyme-labelled antibody to complete the binding reaction, and then spotted on the substrate layer 14. When the immunological reaction layer 16 is superposed on the substrate 14, the measurement is possible in the same procedures described above.

EXAMPLES

Synthesis Example 1
Preparation of GMB Amylase

Maleimide groups were introduced into α-amylase through the following processing steps. To 1 mL of a 10 mg/mL solution of Bacillus subtilis α-amylase solution (in a 0.1M glycerophosphate buffer solution, pH 7.0), 100 μl of a 100 mg/mL solution of GMBS (N-(γ-maleimido-butyryloxy)succinimide; produced by DOJIN KAGAKU) was added and allowed to react at room temperature for 2 hours. The reaction mixture was subjected to the gel filtration through a SEPHADEX G-25 column, and the passing fraction was collected to obtain N-(γ-maleimido-butyryloxy)amidated amylase (GMB amylase). The concentration of thus obtained GMB amylase solution was 1.12 mg/mL.

Synthesis Example 2
Preparation of Anti-human $HbA_{1c}$ monoclonal antibody

A monoclonal antibody IgG against the human $HbA_{1c}$ was prepared through a commonly used process in which immunized cells (spleen cells) obtained by immunizing to mouse were fused with murine myeloma cells, followed by cloning process. In details, 7 μg of natural human hemoglobin $A_{1c}$ dissolved in 1 mM KCN (pH 7.45), 143 μL of RPMI-1640 medium (containing 1 g/L of sodium carbonate, 600 mg/L of L-glutamine and 10 mM of HEPES: pH 6.8) and 200 μL of complete Freund's adjuvant was mixed, and the mixture was administered to a mouse by hypodermic injection as a first priming. The immuno-boosting was carried out every two-weeks. Finally B-lymphocyte was collected from the immunized mouse spleen and fused with murine myeloma cell for cloning. From the resultant clones, the cell line was selected which produced the antibody having specific reactivity to human $HbA_{1c}$ but having substantially no cross-reactivity to other hemoglobin subclasses at all, and thus obtained antibody-forming cells were cultured. By purification of the antibody, the monoclonal antibody specific for human $HbA_{1c}$, anti-human $HbA_{1c}$ IgG, was obtained.

Preparation of Anti-human $HbA_{1c}$ IgG Fab'

Resultant anti-human $HbA_{1c}$ antibody IgG in an amount of 4.4 mg was dissolved in 1 mL of a 0.1M acetate buffer solution (pH 5.5) and then added with 132 μg of activated papain, followed by stirring the mixture at 37° C. for 2 hours. The reaction mixture was then applied to a SUPERDEX-200 gel column, which had been preliminarily equilibrated with a 0.1M phosphate buffer solution (pH 6.0, containing 1 mM EDTA-2Na), followed by elution with the same phosphate buffer solution. The peak fraction of the eluate having the molecular weight of about 100,000 daltons was collected to obtain an anti-human $HbA_{1c}$ IgG F(ab')$_2$. 5 mL of a 0.1M phosphate buffer solution (pH 6.0) containing 2.2 mg of the thus prepared anti-human $HbA_{1c}$ IgG F(ab')$_2$ was added with 100 μl of a 113 mg/mL aqueous solution of 2-mercaptoethylamine-HCl salt to proceed the reaction at 37° C. for 2 hours with stirring. The reaction mixture was subjected to gel filtration by a SEPHADEX G-25, which had been preliminarily equilibrated with a 0.1M glycerophosphate buffer solution (pH 7.0, containing 5 mM EDTA-Ca), to collect the passing fraction. Anti-human $HbA_{1c}$ IgG Fab' (hereinafter referred to as "Fab'") fraction thus prepared was diluted with the same buffer solution to the concentration of the solution to 0.1 mg/mL.

Synthesis Example 3

Preparation of α-Amylase/Fab' Bound

A 0.1 mg/mL solution of anti-human $HbA_{1c}$ IgG Fab' (referred to simply as "Fab'", hereinafter) in an amount of 3.65 mL prepared by Synthesis Example 2 was added with 54 μl of the GBM amylase solution prepared by Synthesis Example 1, and the reaction mixture was maintained at 4° C. for 20 hours to proceed the reaction. The reaction mixture was then applied to a SUPERDEX-200, which had been preliminarily equilibrated with a 0.1M glycerophosphate buffer solution (pH 7.0, containing 0.5 mM EDTA-Ca), to effect elution using the same glycerophosphate buffer solution. The peak fraction at the molecular weight of about 270,000 was collected to obtain an enzyme-labelled antibody (α-amylase/Fab' bound).

Referential Example

Measurement of human-$HbA_{1c}$ (Wet process)

Using the enzyme-labelled antibody, prepared by Synthesis Example 3, human $HbA_{1c}$ was analyzed by a homogeneous enzyme immunoassay. A series of solution of human $HbA_{1c}$ (produced by Exocell, 13 mg/mL, PBS) were prepared by all 3-fold dilution to have concentrations ranging from 0 to 7,000 mg/dL. 50 μL for each of the sequentially diluted solutions was reacted with the α-amylase/Fab' bound at 37° C. for 20 minutes to obtain a series of reaction solutions. On the other hand, one tablet of Neo Amylase Test "Dai-ichi" (produced by Dai-ichi Pure Chemicals Co., Ltd. containing 45 mg of the blue starch and 3 mg of BSA) was dissolved in 4 mL of a 50 mM maleate buffer solution (pH 6.5) to prepare a test solution. 1 mL of the test solution was added to each of the reaction solution to proceed enzymatic reaction at 37° C. for one hour. The reaction was terminated by addition of 5 mL of an aqueous 0.5 N NaOH solution. After agitating, the solution was subjected to centrifugation at 3,000 rpm for 5 minutes, and the supernatant was taken out. The supernatant was subjected to light absorption analysis at 620 nm to determine the quantity of blue dyestuff which had been solubilized by the enzymatic reaction and dissolved in the supernatant.

Figure 3:
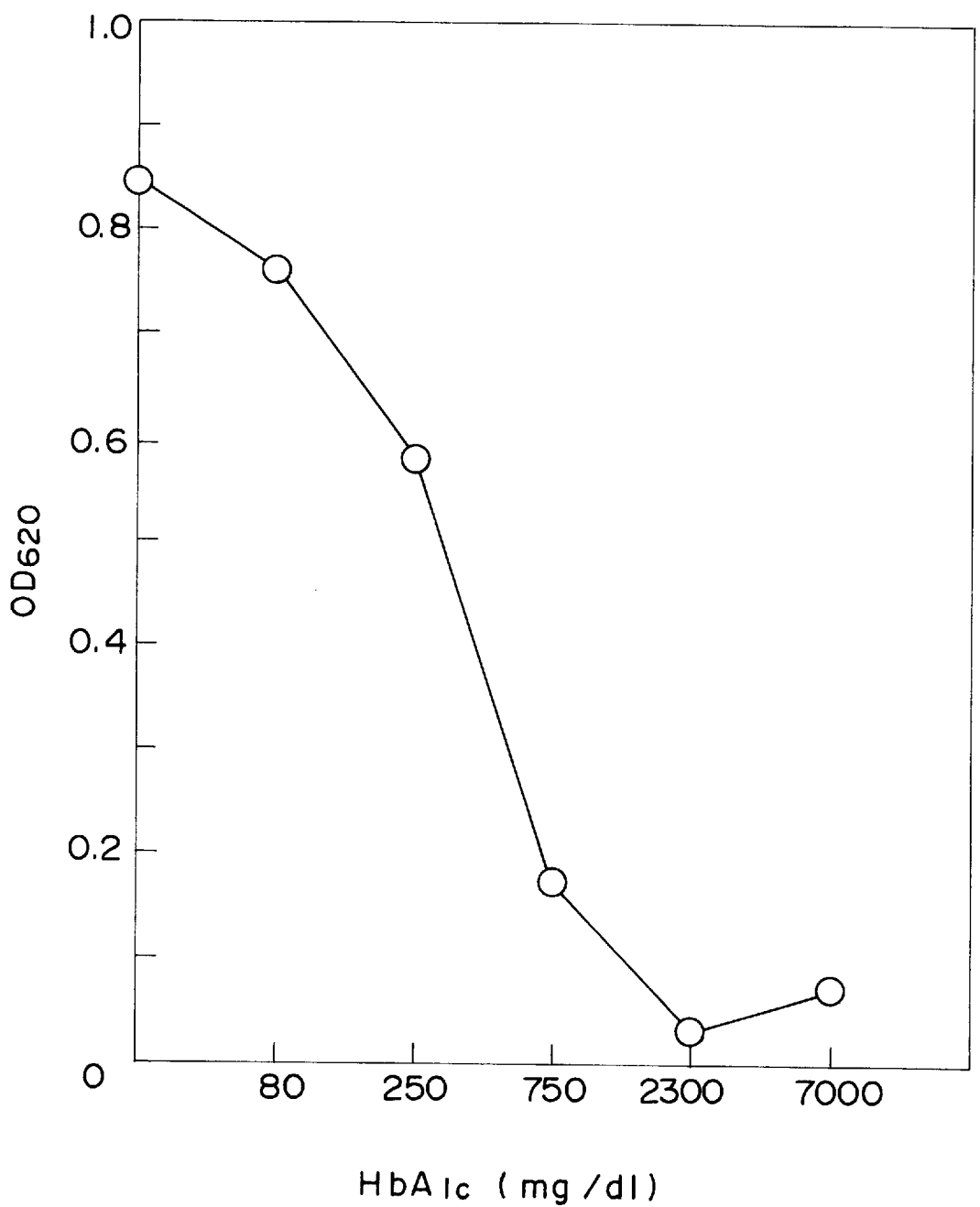
FIG. 3 is a graphic representation showing the calibration curve in a reference example (wet method)

FIG. 3 shows the interrelation between the absorbance observed and the concentration of human $HbA_{1c}$. As shown in FIG. 3, it was experimentally proved that the amount of human $HbA_{1c}$ is detectable as the decreasing in enzymatic activity of the α-amylase, labelling enzyme.

Example 1

On a colorless and transparent polyethylene terephthalate (PET) sheet (support) coated with a gelatin undercoating and having a thickness of 180 μm, coated was a reagent solution containing a cross-linking reagent, followed by drying, to form a reagent layer so that respective components had the coverages as set forth below.

| | |
|---|---|
| Alkaline-treated Gelatin | 14.5 g/m$^2$ |
| Nonylphenoxypolyethoxyethanol (Containing 9 to 10 (average) of Oxyethylene Units) | 0.2 g/m$^2$ |
| Glucose Oxidase | 5,000 U/m$^2$ |
| Peroxidase | 15,000 U/m$^2$ |
| Glucoamylase | 5,000 U/m$^2$ |
| 2-(4-hydroxy-3,5-dimethoxyphenyl)-4-[4-(dimethylamino)phenyl]-5-phenetyl-imidazole (Leuco Dye) Acetate | 0.38 g/m$^2$ |
| Bis[(vinylsulfonylmethylcarbonyl)amino]-methane | 0.1 g/m$^2$ |

An adhesive layer was coated on the reagent layer to have the following coverage, and then dried.

| | |
|---|---|
| Alkaline-treated Gelatin | 14.5 g/m$^2$ |
| Bis[(vinylsulfonylmethylcarbonyl)amino]-methane | 0.1 g/m$^2$ |

Then, an aqueous solution containing the following reagent was coated over the surface of the adhesive layer to have the following coverages to swell the gelatin layer and a tricot knitted cloth made by knitting PET spun yarn of 36 gage corresponding to 50 deniers and having a thickness of about 250 μm was laminated thereon, by pressing with a uniform light pressure to form a porous spreading layer.

| | |
|---|---|
| Nonylphenoxypolyethoxyethanol (Containing 9 to 10 (average) of Oxyethylene Units) | 0.15 g/m$^2$ |
| Bis[(vinylsulfonylmethylcarbonyl)amino]-methane | 0.4 g/m$^2$ |

Thereafter, a substrate layer was formed by coating a substrate, followed by drying, to have the following coverages, whereby a multi-layered analysis element for the quantitative analysis of $HbA_{1c}$ was prepared.

| | |
|---|---|
| Carboxymethylated Starch | 5 g/m$^2$ |
| Nonylphenoxypolyethoxyethanol (Containing 9 to 10 (average) of Oxyethylene Units) | 0.2 g/m$^2$ |

The thus prepared element was cut into tips each having 15 mm square, and each tip was placed in a slide frame described in Unexamined Japanese Patent Publication No. 63452/1982 to prepare a multi-layered dry slide 1 for the analysis of hemoglobin $A_{1c}$ according to this example.

Test for Appraisal of the Properties

The α-amylase/Fab' bound prepared by Synthesis Example 3 was added to a 50 mM glycerophosphate buffer solution (pH 7) containing a predetermined quantity of human $HbA_{1c}$ to prepare a solution containing the bound in a concentration of 0.1 mg/mL. The thus prepared solution was incubated at 37° C. for 20 minutes. The incubated solution in an amount of 10 μl was spotted on the aforementioned slide 1 which was maintained at 37° C., and the optical density of the reflected light having a wavelength of 650 nm was measured from the PET support side. The difference in optical density ($\Delta D_{6-4}$) of the reflected lights measured respectively after the lapse of 4 minutes and 6 minutes was determined.

A calibration curve was prepared based on the result of determination. The calibration curve thus prepared is shown in FIG. 4.

Example 2

Similar to Example 1, a multi-layered analysis element having a tricot knitted cloth layer was prepared. On the tricot knitted cloth layer, which served both as a substrate layer and a spreading layer, coated was a solution of the enzyme-labelled antibody (α-amylase/Fab' bound) prepared by Synthesis Example 3 in ethanol to have a coverage of 3 mg/m², followed by drying, to prepare a multi-layered immunoassay slide 2 for the analysis of $HbA_{1c}$.

Test for Appraisal of the Properties

10 μL of 50 mM glycerophosphate buffer solution containing a known quantity of human $HbA_{1c}$ was spotted on the slide 2. The slide was maintained at 37° C., and the optical density of the reflected light having a wavelength of 650 nm was measured from the PET support side. Measurement was carried out to know the difference in optical density ($\Delta OD_{6-4}$) between the optical density of the reflected light measured after the lapse of 4 minutes from the spotting and the optical density of the reflected light measured after the lapse of 6 minutes from spotting. A calibration curve was prepared from the result of measurement. It should be appreciated from the calibration curve of the slide 2 of the Example 2 shown in FIG. 5 that the dry immunoassay element for analyzing hemoglobin $HbA_{1c}$ according to the present invention can be used for quantitative analysis of hemoglobin $HbA_{1c}$ to give accurate result.

Example 3

A multi-layered analysis slide 3 for analyzing hemoglobin $HbA_{1c}$ was prepared in the same way as Example 2.

Test for Appraisal of the Properties

Figure 6:
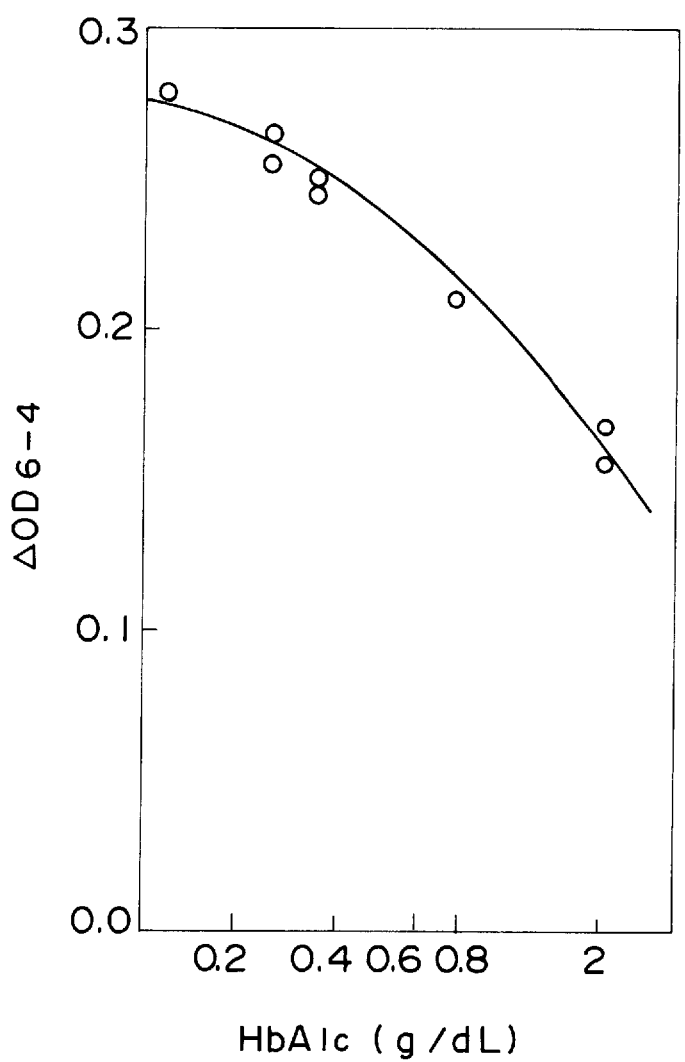
FIG. 6 is a graphic representation showing the calibration curve of human $HbA_{1c}$ when the analysis element of Example 3 is used.

One volume of human whole blood containing known amounts of hemoglobin $A_{1c}$ and total hemoglobin was mixed and diluted with 20 volumes of a 50 mM glycerophosphate buffer solution of pH 7; thereby hemolysis was made. This diluted solution in a volume of 10 μL was spotted on the slide 3 and maintained at 37° C., and the optical density of the reflected light having a wavelength of 650 nm was measured from the PET support side. The difference in optical density ($\Delta OD_{6-4}$) of the reflected lights measured respectively after the lapse of 4 minutes and 6 minutes from the spotting, based on which a calibration curve was prepared. From the result of the slide 3 of the Example 3 as shown in FIG. 6, it is apparent that the dry immunoassay element according to the present invention can be used for quantitative analysis of the hemoglobin $A_{1c}$ in excellent accuracy.

Figure 7:
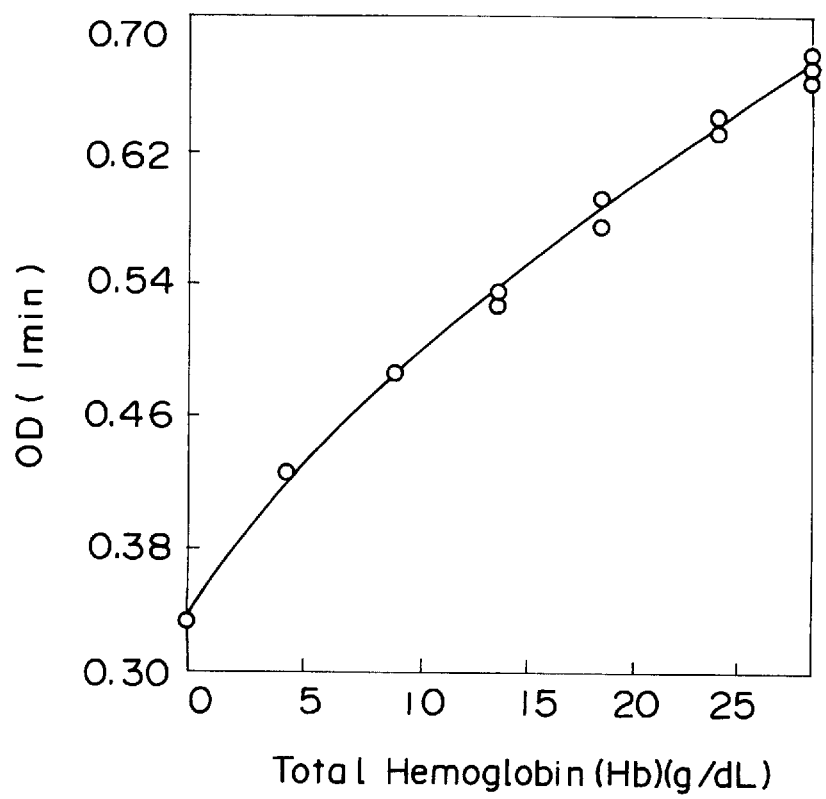
FIG. 7 is a graphic representation showing the calibration curve of human total Hb when the analysis element of Example 3 is used.

In the same time, the optical density of the reflected light having a wavelength of 540 nm was measured from the support side of slide 3 was measured. The optical density (OD) of the reflected light one minute later after the spotting is shown in FIG. 7. As the calibration curve of FIG. 7 indicates, the dry immunoassay element according to the present invention can be apparently used for quantitative analysis of not only the glycated hemoglobin but also the total hemoglobin Hb in excellent accuracy.

Figure 8:
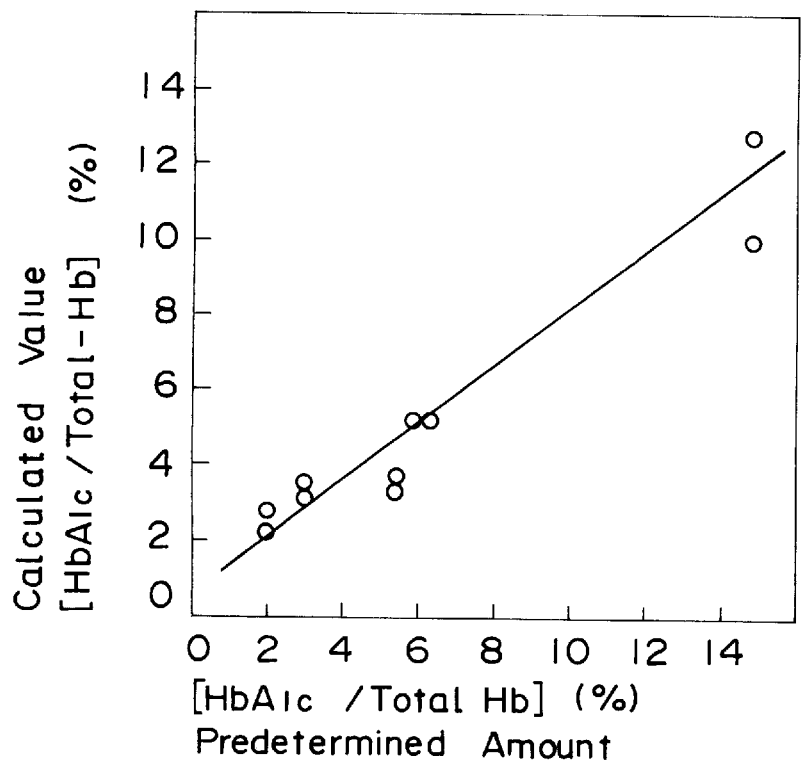
FIG. 8 is a graphic representation showing the correlation between calculated values of $[HbA_{1c}/\text{total-Hb}]$ obtained from the immunoassay element of Example 3 and predetermined values of $[HbA_{1c}/\text{total-Hb}]$.

As shown, both hemoglobin $A_{1c}$ and total hemoglobin Hb were simultaneously able to be detected and analyzed quantitatively in Example 3. Thereby, the glycosylation level of hemoglobin, which is defined as the ratio of $HbA_{1c}$ to total Hb and an important index for diabetes disease, can be easily and rapidly determined by simple calculation. Using plural samples having various glycosylation levels of hemoglobin, a correlation graph was prepared against predetermined $HbA_{1c}$/total-Hb (FIG. 8). The excellent correlation was obtained and it was proved that the dry immunoassay element for analyzing hemoglobin $A_{1c}$ according to the present invention can be used for quantitative analysis of $HbA_{1c}$/total-Hb to give accurate result.

What is claimed is:

1. An analysis method for simultaneously analyzing both amounts of glycated hemoglobin and total hemoglobin in a single aqueous liquid sample so as to calculate glycated hemoglobin content ratio in the sample, the method comprising the steps of:

(a) mixing the entire single aqueous liquid sample containing hemoglobin including glycated hemoglobin with an enzyme-labelled antibody against the glycated hemoglobin to allow the antigen-antibody reaction between the glycated hemoglobin and the enzyme-labelled antibody;

(b) supplying the reaction mixture after the completion of said antigen-antibody reaction to a substrate layer containing a non-diffusible substrate which forms a diffusible material in the presence of the enzyme of said enzyme-labelled antibody, the activity of said enzyme being effected relative to the steric hindrance due to said antigen-antibody reaction;

(c) allowing said diffusible material formed in said substrate layer to migrate to a reagent layer which contains a reagent composition for reacting with the diffusible material to form a dye, the formed dye being detectable colorimetrically in a wavelength range which is not affected by an absorption spectrum of the hemoglobin, the diffusion resistance of said reagent layer being larger than the diffusion resistance of said substrate layer;

(d) measuring colorimetrically the amount of the formed dye in the reagent layer to analyze quantitatively the amount of glycated hemoglobin contained in the sample;

(e) measuring the amount of the total hemoglobin retained in the substrate layer by the colorimetrical determination at a wavelength range in which the hemoglobin has its inherent absorption, to analyze quantitatively the amount of total hemoglobin in the sample; and (f) calculating the ratio of the glycated hemoglobin amount to the total hemoglobin amount so as to determine the glycated hemoglobin content ratio in the sample.

2. The analysis method according to claim 1, wherein said glycated hemoglobin is glycosylated hemoglobin $HbA_{1c}$.

3. The analysis method according to claim 1, wherein the colorimetric determination of total hemoglobin in said step (e) is done precedently to the formation of said pigment in the reagent layer in said step (c).

4. The analysis method according to claim 1, wherein said reagent layer is composed of a non-porous medium and said substrate layer is composed of a porous medium.

5. The analysis method according to claim 1, wherein said reagent layer contains a fragmenting enzyme for further fragmenting said diffusible material into a lower molecular weight product.

6. The analysis method according to claim 5, wherein said non-diffusible material is a high polymer polysaccharide, said enzyme of the enzyme-labelled antibody is an endo-active glucosidase, and said fragmenting enzyme is an exo-active glucosidase.

7. The analysis method according to claim 6, wherein said lower molecular weight product is glucose.

8. The analysis method according to claim 7, wherein said reagent composition reacts with said lower molecular weight product to form a peroxide.

9. The analysis method according to claim 8, wherein said reagent composition contains a leuco dye.

10. The analysis method according to claim 9, wherein said reagent layer contains a hydrophilic binder, and wherein said reagent composition contains a dispersion of a solution of said leuco dye in a water-insoluble solvent in the hydrophilic binder.

11. The analysis method according to claim 10, wherein said reagent composition contains glucose oxidase, peroxidase and the leuco dye.

12. An analysis method for simultaneously analyzing both amounts of glycated hemoglobin and total hemoglobin in a single aqueous liquid sample so as to calculate glycated hemoglobin content ratio in the sample, the method comprising the steps of:

(a) mixing the entire single aqueous liquid sample containing hemoglobin including glycated hemoglobin with an enzyme labelled antibody against the glycated hemoglobin to allow the antigen-antibody reaction between the glycated hemoglobin and the enzyme-labelled antibody;

(b) supplying the reaction mixture after the completion of said antigen-antibody reaction to a substrate layer containing a non-diffusible substrate which forms a diffusible material in the presence of the enzyme of said enzyme-labelled antibody, the activity of said enzyme being effected relative to the steric hindrance due to said antigen-antibody reaction, the diffusible material being detectable colorimetrically in a wavelength range which is not affected by an absorption spectrum of the hemoglobin;

(c) allowing said diffusible material formed in said substrate layer to migrate to a detection layer, the diffusion resistance of said detection layer being larger than the diffusion resistance of said substrate layer;

(d) measuring colorimetrically the amount of the diffusible material in the detection layer to analyze quantitatively the amount of glycated hemoglobin contained in the sample;

(e) measuring the amount of the total hemoglobin retained in the substrate layer by the colorimetrical determination at a wavelength range in which the hemoglobin has its inherent absorption, to analyze quantitatively the amount of total hemoglobin in the sample; and (f) calculating the ratio of the glycated hemoglobin amount to the total hemoglobin amount so as to determine the glycated hemoglobin content ratio in the sample.

13. The analysis method according to claim 12, wherein said non-diffusible substrate is a dye-starch.

14. The analysis method according to claim 12, wherein said detection layer is composed of a non-porous medium and said substrate layer is composed of a porous medium.

15. The analysis method according to claim 12, wherein said glycated hemoglobin is glycosylated hemoglobin $HbA_{1c}$.

16. The analysis method according to claim 12, wherein the colorimetric determination of total hemoglobin in said step (e) is done precedently to the migration of said diffusible material to the detection layer in said step (c).

* * * * *